(«12») United States Patent
Stein et al.

(10) Patent No.: US 9,125,798 B2
(45) Date of Patent: Sep. 8, 2015

(54) SYSTEMS AND METHODS FOR REMINDING A PATIENT TO CONSUME A MEDICATION

(71) Applicants: AdhereTech Inc., New York, NY (US); The Board of Trustees of the University of Alabama, for and on behalf of the University of Alabama in Huntsville, Huntsville, AL (US)

(72) Inventors: Joshua Stein, Boca Raton, FL (US); John Langhauser, Basking Ridge, NJ (US); Michael Morena, Huntsville, AL (US); Emil Jovanov, Huntsville, AL (US)

(73) Assignees: AdhereTech Inc., New York, NY (US); The Board of Trustees of the University of Alabama, for and on behalf of the University of Alabama, Huntsville, AL (US)

( * ) Notice: Subject to any disclaimer, the term of this patent is extended or adjusted under 35 U.S.C. 154(b) by 0 days.

(21) Appl. No.: 14/273,249

(22) Filed: May 8, 2014

(65) Prior Publication Data
US 2014/0347175 A1    Nov. 27, 2014

Related U.S. Application Data

(62) Division of application No. 13/775,671, filed on Feb. 25, 2013, now Pat. No. 8,754,769.

(60) Provisional application No. 61/752,679, filed on Jan. 15, 2013, provisional application No. 61/603,353, filed on Feb. 26, 2012.

(51) Int. Cl.
*G08B 1/00*        (2006.01)
*A61J 7/04*        (2006.01)
*A61J 1/03*        (2006.01)
*B65D 25/00*       (2006.01)
*G06F 19/00*       (2011.01)
*A61J 7/02*        (2006.01)
*G06Q 10/10*       (2012.01)

(52) U.S. Cl.
CPC ....... *A61J 7/0409* (2013.01); *A61J 1/03* (2013.01); *A61J 7/02* (2013.01); *A61J 7/04* (2013.01); *A61J 7/0418* (2015.05); *A61J 7/0481* (2013.01); *B65D 25/00* (2013.01); *G06F 19/3462* (2013.01); *A61J 2007/0418* (2013.01); *A61J 2200/30* (2013.01); *A61J 2200/76* (2013.01); *G06Q 10/10* (2013.01)

(58) Field of Classification Search
CPC ............................. A61J 7/0409; G06Q 10/10
USPC .......... 340/309.7, 309.16, 540, 541, 687, 5.2, 340/5.82; 700/231, 232, 236, 242
See application file for complete search history.

(56) References Cited

U.S. PATENT DOCUMENTS

2003/0063522 A1\*  4/2003  Sagar ............................. 368/10
2005/0088289 A1\*  4/2005  Rochkind ................ 340/309.16
2007/0016443 A1\*  1/2007  Wachman et al. ................ 705/2

*Primary Examiner* — Tai T Nguyen
(74) *Attorney, Agent, or Firm* — Mintz Levin Cohn Ferris Glovsky and Popeo, P.C.

(57) ABSTRACT

Systems and methods are provided for determining whether and/or when a patient is taking his or her medication and, when appropriate, providing reminders and/or alerts to the patient to improve adherence to a medication regimen. In some embodiments, a medication container is provided that includes a capacitance sensor for sensing the contents of the medication container (e.g., pill count or quantity of liquid medication). The capacitance sensor may include interleaved or interdigitated electrodes oriented vertically, horizontally, or angularly (e.g., diagonally) relative to an axis of the medication container. Reminders and/or alerts to the patient may be triggered based at least in part on the contents of the medication container, when a cap of the container was last opened and/or closed, the location of the medication container, and/or the container's surroundings.

6 Claims, 11 Drawing Sheets

116

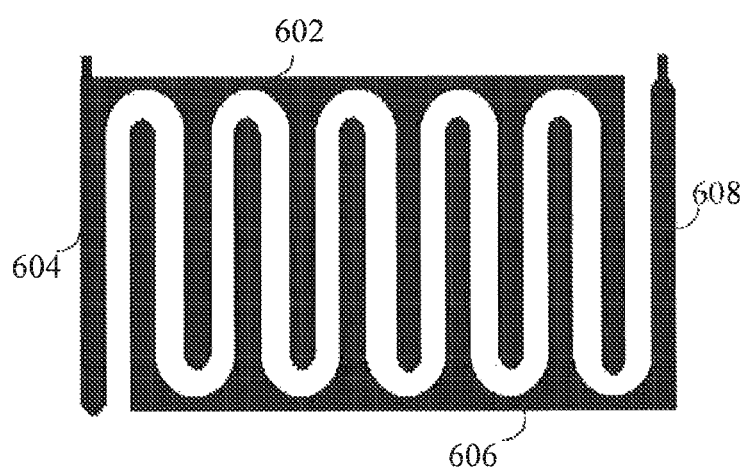
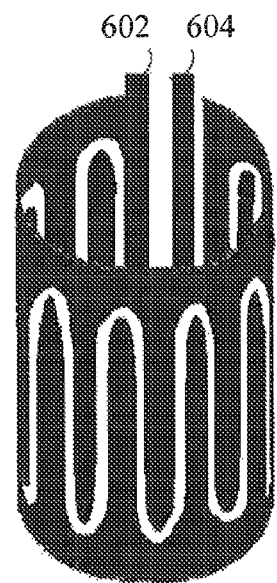
FIG. 6A
FIG. 6B

SYSTEMS AND METHODS FOR REMINDING A PATIENT TO CONSUME A MEDICATION

CROSS REFERENCE TO RELATED APPLICATIONS

This application is a divisional of U.S. application Ser. No. 13/775,671, filed on Feb. 25, 2013, now U.S. Pat. No. 8,754, 796, which claims the benefit under 35 U.S.C. §119(e) of U.S. Provisional Patent Application Nos. 61/603,353, filed on Feb. 26, 2012, and 61/752,679, filed on Jan. 15, 2013, which are hereby incorporated by reference herein in their entireties.

FIELD OF THE EMBODIMENTS

Embodiments of the present disclosure relate to systems and methods for determining whether and/or when a patient is taking his or her medication and, when appropriate, providing appropriate reminders and/or alerts to the patient to improve adherence to a medication regimen. In some embodiments, a medication container is provided that includes a capacitance sensor for sensing the contents of the medication container (e.g., pill count or quantity of liquid medication). In particular embodiments, the capacitance sensor includes interleaved or interdigitated electrodes oriented vertically, horizontally, or diagonally relative to an axis of the medication container or positioned in any other suitable manner for measuring the capacitance attributable to the container contents. In some embodiments, the systems and methods described herein trigger reminders and/or alerts to the patient based at least in part on data indicative of the contents of the medication container, when a cap of the container was last opened and/or closed, the location of the medication container, and/or the container's surroundings.

BACKGROUND

It is estimated that approximately 133 million people suffer from at least one chronic illness in the United States alone, and that chronic illnesses lead to approximately seven out of every ten deaths in the United States each year. Medications are often prescribed to alleviate and treat these illnesses, yet go unconsumed. With current levels of adherence to medication regimens at or below 50%, patients are not properly treating their chronic diseases, even though many have access to preventative or palliative medications. Tragically, a primary reason for patients not taking their medication is forgetfulness.

In view of the foregoing, what are needed are systems and methods for increasing patient adherence to medication regimens. Increasing patient adherence promises to improve patient outcomes and quality of life.

SUMMARY

According to one aspect of the present disclosure, a medication container is provided that includes a housing (e.g., bottle) for medication and a cap removably coupled to the housing. In some embodiments, the medication container includes a cap sensor configured to sense opening and/or closing of the cap. Alternatively or additionally, in some embodiments, the medication container includes a measurement sensor (e.g., capacitance sensor or weight sensor) coupled to the housing for sensing a quantity of medication within the housing. In some embodiments, the medication container includes a processor configured to trigger a reading of the measurement sensor based at least in part on a status of the cap sensor (e.g., triggering a reading of the measurement sensor immediately after, or 5 or 10 seconds after, the cap sensor indicates that the cap is closed).

In some embodiments, the medication container includes a transmitter (e.g., transceiver) for wirelessly transmitting to a remote computer data regarding a reading of the measurement sensor (e.g., data indicative of a number of pills or quantity of liquid medication within the medication container).

In some embodiments, the medication container includes a wireless receiver and/or an alert (e.g., one or more light sources, graphical displays, text displays, and/or speakers). For example, the wireless receiver may be configured to receive an activation command from, or otherwise initiated by, a remote computer (e.g., a backend system or user computer such as a cellular phone running a suitable communications application for communicating with the medication container). A processor within the medication container may activate the alert based at least in part on the receipt of the activation command by the wireless receiver.

According to another aspect according to some embodiments of the present disclosure, a medication container is provided that includes a housing for medication and a capacitance sensor coupled to the housing for sensing a capacitance corresponding to a quantity of the medication within the housing. In some embodiments, the capacitance sensor includes multiple conductive electrodes arranged in an interleaved or interdigitated pattern. In some embodiments, the medication container includes a capacitance to digital converter for converting the capacitance sensed by the capacitance sensor into digital data.

In some embodiments, the conductive electrodes of a capacitance sensor include a first conductive electrode in electrical communication with a first conductive terminal, and second and third conductive electrodes in electrical communication with a second conductive terminal. The first conductive electrode may be positioned in between the second and third conductive electrodes. The capacitance attributable to the quantity of the medication within the housing may be sensed in between the first conductive terminal and the second conductive terminal.

The electrodes of a capacitance sensor may have any suitable size, shape, and/or configuration. In some embodiments, the conductive electrodes of a capacitance sensor include regularly-spaced conductive electrodes in an interleaved pattern. In some embodiments, the interleaved pattern of conductive electrodes includes rectangularly shaped or generally rectangularly shaped conductive electrodes. In some embodiments, one or more of the electrodes is positioned in parallel, generally parallel, perpendicular, or generally perpendicular to a vertical axis of the medication container when the medication container is in an upright position. In some embodiments, one or more of the electrodes is positioned diagonal, generally diagonal, or in another angular relationship (e.g., angled between 35 to 55 degrees) relative to a vertical axis of the medication container when the medication container is in an upright position.

In some embodiments, the capacitance sensor is configured such that the capacitance corresponding to the medication varies linearly or generally linearly to the quantity of medication within the housing.

In some embodiments, the capacitance corresponding to the quantity of the medication varies by between 10 femto-Farads (fF) to 100 fF per pill that is added to or removed from the housing.

In some embodiments, the capacitance corresponding to the quantity of the medication varies by between 250 femto- Farads (fF) to 450 fF per milliliter of liquid medication that is added to or removed from the housing.

According to yet another aspect according to some embodiments of the present disclosure, systems and methods are provided for reminding a patient to consume a medication. The system may include computer memory configured to store data indicative of a medication regimen associated with a patient. The system may also include one or more computers configured to receive communications from a medication container associated with the patient. The one or more computers may compare data indicative of when a communication was last received by the one or more computers from the medication container (e.g., a communication indicating that the patient consumed his or her medication) to the data indicative of the medication regimen associated with the patient. Based at least in part on the comparison, the one or more computers may trigger a reminder to the patient to consume the medication.

In some embodiments, the system and method may include one or more computers configured to receive a communication from the medication container indicating a quantity of medication within the medication container at a particular time. The one or more computers may compare the data indicative of the quantity of the medication within the container to data indicative of a medication regimen associated with the patient. Based at least in part on the comparison, the one or more computers may trigger a reminder to the patient to consume the medication.

The foregoing summary is only illustrative of the embodiments disclosed herein. Additional embodiments of the present disclosure, including systems, methods, apparatus, computer readable media, and means for performing the functions disclosed herein, are further described in the detailed description and shown in the figures.

BRIEF DESCRIPTION OF THE DRAWINGS

Various aspects and embodiments of the present disclosure will be described with reference to the following figures, which are not necessarily drawn to scale and are not intended to be limiting. Items appearing in multiple figures are indicated by the same reference number or character in all the figures in which they appear.

FIGS. 6A and 6B illustrate another capacitance sensor that includes vertically-oriented interleaved or interdigitated electrodes according to some embodiments of the present disclosure;

DETAILED DESCRIPTION OF EMBODIMENTS

Figure 1:
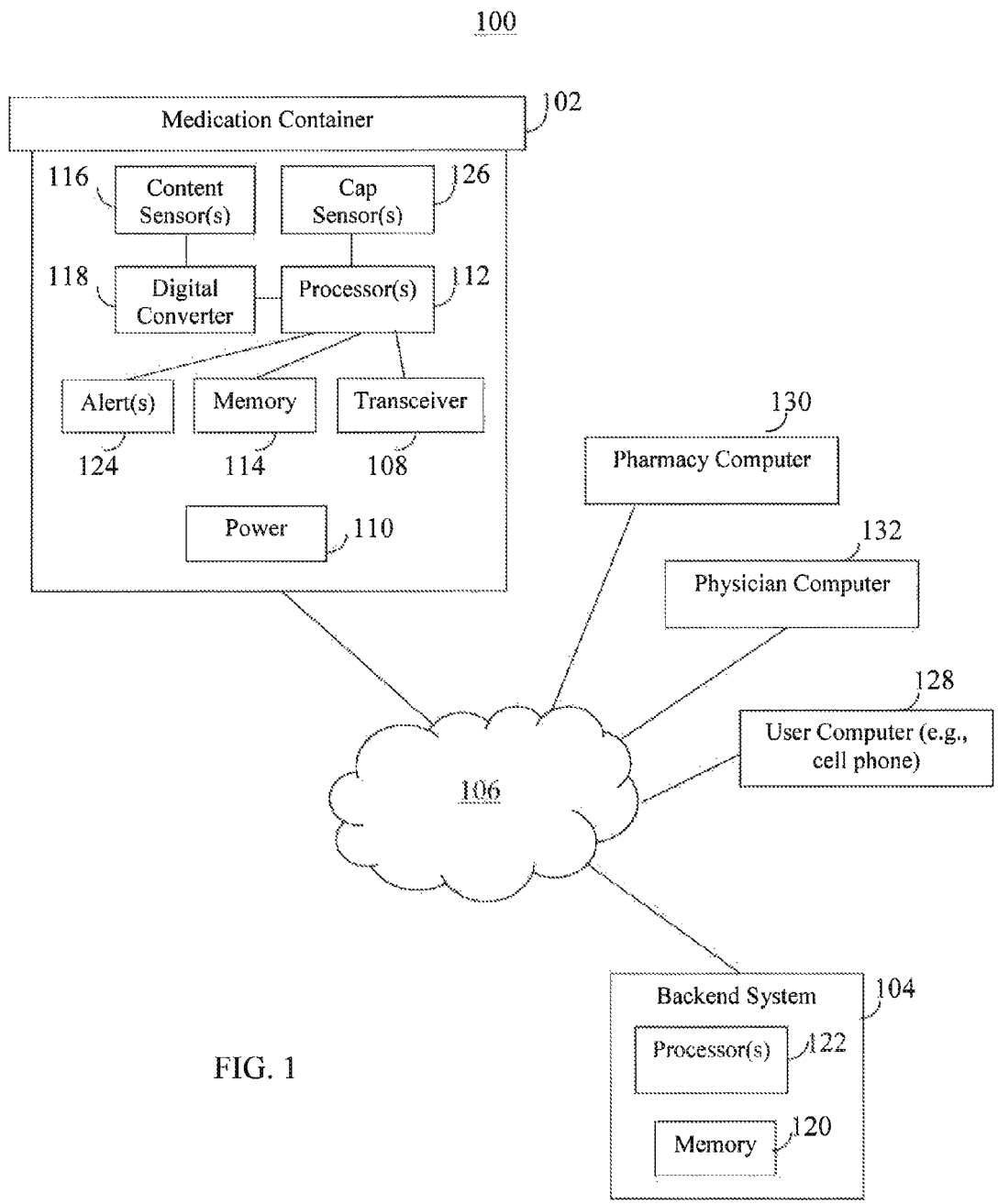
FIG. 1 is a block diagram of an illustrative system for determining the contents of a medication container and/or providing patients with reminders and/or alerts to take their medication according to some embodiments of the present disclosure.

The present disclosure generally relates to systems and methods for increasing patient adherence to medication regimens. FIG. 1 is a block diagram of an illustrative system 100 for determining the contents of a medication container 102 and/or providing patients with reminders and/or alerts to take their medication according to some embodiments of the present disclosure. Medication container 102 may be a bottle or other container for housing prescription or non-prescription pills or liquid medication. In some embodiments, system 100 includes medication container 102 and backend system 104, which may include one or more servers. In some embodiments, system 100 includes user computer 128 (e.g., cellular phone, tablet computer, laptop computer, personal digital assistant (PDA), or desktop computer), pharmacy computer 130, and/or physician's computer 132.

Medication container 102 may be communicatively coupled via communications capability 106 to one or more (e.g., all) of backend system 104, user computer 128, pharmacy computer 130, and/or physician's computer 132. For example, in some embodiments, medication container 102 includes a wireless transmitter or transceiver 108 for transmitting and/or receiving communications, including, for example, a cellular modem (e.g., Telit CC864-Dual, Sierra Wireless 6087 or 5011, or Janus CDMA Terminus Plug-In CDMA864C). Communications capability 106 may be a wireless link (e.g., radio frequency (RF) link, Bluetooth link, 2G link, 3G link), other communications link, or combination of communication links. In various embodiments, medication container 102 may utilize the same or different communications links for communicating with different computers (e.g., utilizing different communications links for communicating with backend system 104 and user computer 128).

In some embodiments, medication container 102 may communicate with backend system 104 directly via one or more communications links of communications capability 106. In other embodiments, communications capability 106 may include one or more intermediate devices that enable communications between medication container 102 and backend system 104. For example, in some embodiments, communications capability 106 may include a dedicated base station within the user's home (e.g., a base station configured to plug into a wall outlet) or other intermediate computer(s) for enabling communications with backend system 104 (e.g., cell phone, personal digital assistant (PDA), or general purpose computer such as a desktop computer running a communications application). In such embodiments, medication container 102 may communicate with an intermediate device via a wired or wireless connection (e.g., USB connection, Bluetooth connection, or other wired or wireless connection). In turn, the intermediate device(s) may communicate with backend system 104 via suitable wired and/or wireless connection(s) (e.g., cellular network, local area network (LAN), wide area network such as the Internet, and/or public switched telephone network (PSTN)). In some embodiments, the intermediate device(s) may communicate to backend system 104 some or all of the data communicated by medication container 102 and/or other data.

Medication container 102 may include one or more components for enabling its operation, intelligence, and/or communication with backend system 104 and/or other computer(s). For example, medication container 102 may include local power source 110 for powering electrical circuitry within the container (e.g., lithium battery, lithium-polymer battery, graphene battery, super-capacitor, and/or associated charging circuitry), computer(s) or processor(s) 112 (e.g., microcontroller such as ATMEL ATmega32U4, ATMELmega328, or PIC16F57), memory 114 (e.g., random access memory (RAM)), and/or one or more antennas included as part of transceiver block 108 (e.g., 800/1900 MHz antenna).

In some embodiments, medication container 102 may include one or more sensors 116 for sensing a quantity of medication within the container (e.g., pill count or quantity of liquid medication). For example, in some embodiments, medication container 102 may include at least one capacitance sensor.

In some embodiments, medication container 102 includes a capacitance sensor that includes interleaved or interdigitated electrodes for sensing a quantity of medication within the container. For example, the capacitance sensor may include one or more conductive electrodes in electrical communication with a first conductive electrical terminal (e.g., 1, 2, 3, 4, 5, 6, 7, 8, 9, 10, 20, 30, 50, or 100 electrodes, or more, or any number of electrodes or range of numbers of electrodes in between). One or more of these electrodes may be interlaced (e.g., in an opposing comb configuration) with conductive electrode(s) associated with a second conductive electrical terminal (e.g., 1, 2, 3, 4, 5, 6, 7, 8, 9, 10, 20, 30, 50, or 100 electrodes, or more, or any number of electrodes or range of numbers of electrodes in between). For example, in some embodiments, an electrode in electrical communication with a first electrical terminal may be positioned between two electrodes in electrical communication with a second electrical terminal. A measurement indicative of the capacitance between the first and second electrical terminals may correspond to a quantity of medication within medication container 102 (e.g., number of pills or quantity of liquid medication). In some embodiments, the capacitance may be measured between the terminals upon application of an excitation signal at one or more of the terminals, such as, for example, an excitation signal of 3 volts or less and 250 kilohertz (kHz) or less (e.g., 32 kHz or 1 kHz).

In some embodiments, at least a portion (e.g., all) of the interleaved or interdigitated electrodes of a capacitance sensor 116 may be oriented horizontally, vertically, diagonally (45 degrees), or in any other angular relationship(s) (e.g., between 0 and 30, between 30 and 60 degrees, or between 60 and 90 degrees, or any other value or range of values in between) relative to a normal and upright position of medication container 102. In some embodiments, the electrodes of capacitance sensor 116 may be shielded (e.g., with copper foil), for example, to improve noise immunity.

When content sensor 116 within medication container 102 is a capacitance sensor, it may provide a capacitance reading (e.g., analog reading) that is converted into digital data via a suitable capacitance to digital converter 118 in medication container 102 (e.g., Analog Devices AD7746). In some embodiments, the digital data may be stored in memory 112. Medication container 102 may transmit the digital data and/or related information, which corresponds to a quantity of medication in container 102, to backend system 104 and/or other computer(s) (e.g., patient's cellular phone 128) via communications capability 106.

In some embodiments, backend system 104 and/or other computer(s) (e.g., patient's cellular phone 128) may receive data from medication container 102 corresponding to measurement(s) by sensor(s) 116 in medication container 102 and convert it into quantit(ies) of medication, such as, for example, one or more pill counts or quantities of liquid medication. For example, backend system 104 and/or other computer(s) may include memory 120 for storing conversion data correlating capacitance and/or other readings to pill counts or quantities of liquid medication for various types of medication, including, for example, pill size, shape, density, composition, and/or capacitance linear regression constants. One or more computer(s) or processor(s) 122 in backend system 104 and/or other computer(s) may utilize the conversion data to convert the capacitance measurement(s) into one or more quantities of medication. In other embodiments, processor(s) 112 within medication container 102 may convert capacitance measurement(s) into one or more quantities of medication, for example, before transmitting digital data corresponding to the quantit(ies) to backend system 104 and/or other computer(s). In some embodiments, medication container 102, backend system 104, and/or other computer(s) (e.g., patient's cellular phone 128) may trigger one or more reminders and/or alerts to the patient to take medication based at least in part on data received as a result of or derived from capacitance measurement(s) by sensor(s) 116. For example, an application running on backend system 104 or a patient's cellular phone or tablet computer 128 may receive (e.g., from medication container 102) data indicative of the medication contents of medication container 102, and may initiate one or more reminders and/or alerts to the patient based at least in part on the data.

Capacitance sensor(s) 116 for medication container 102 may be formed and/or utilized in any suitable manner. For example, in some embodiments, conductive electrodes (e.g., plates) for the capacitance sensor may be formed from an adhesive conductor (e.g., copper tape). In some embodiments, electrodes for the capacitance sensor may be formed from one or more flexible multi-layer printed circuit boards (PCBs). In some embodiments, a dual layer flexible PCB may be utilized to measure capacitance on one layer and act as a grounded electrical shield on the other layer (a capacitance subtractor). In some embodiments, the exterior of a volume being used to measure capacitance may be grounded. A grounding shield according to some embodiments of the present disclosure adds a static capacitance to the capacitance that a measurement device (e.g., digital converter 118) already reads between the two sense electrodes. System 100 may cancel out the static capacitance as part of the capacitance-to-digital-acquisition such that full dynamic range of converter 118 remains available for sensing medication. The grounding electrode(s) (e.g., plate(s)) may advantageously eliminate any variation in the capacitance reading that a nearby object or hand might cause because all of the electric (E)-field lines of the capacitance inside the bottle may terminate inside of the shield, such that anything outside the shield does not perturb (or does not substantially perturb) the field lines. In some embodiments, electrodes (e.g., copper plates or portions of flexible PCB(s)) for use with capacitance measurements may be over-molded with a plastic injection process. In some embodiments, conductive (e.g., copper) plates may be inserted inside of medication container 102 for use in measuring a quantity of medication. In some embodiments, conductors for one or more sensors 116 may be imbedded in or otherwise integrated with one or more walls of medication container 102 (e.g., slipped or positioned in between a small passage between two plastic walls).

Figure 9:
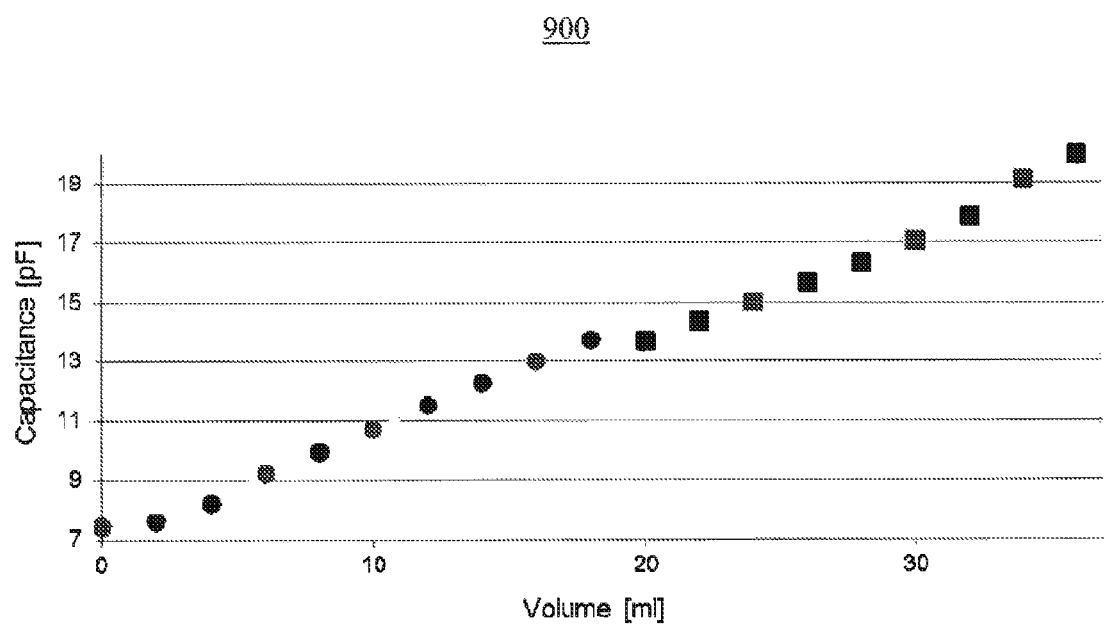
FIG. 9 is a graph of measured capacitance versus volume of liquid medication in a medication container as measured by a capacitance sensor in accordance with an embodiment of the present disclosure.
Figure 10A:
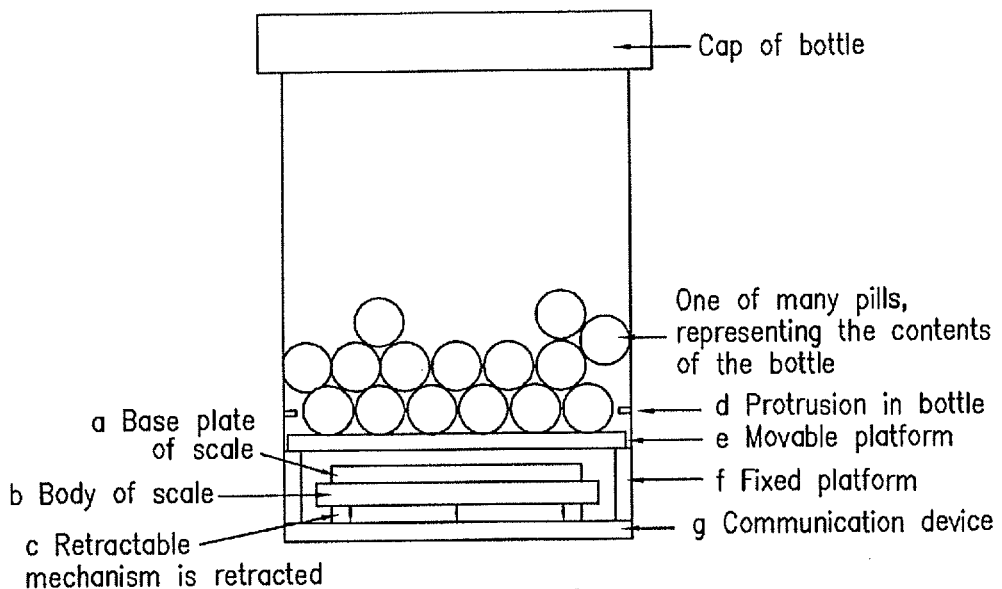
FIGS. 10A and 10B illustrate a medication container that includes a weight sensor for measuring the weight of medication within the container according to some embodiments of the present disclosure.
Figure 10B:
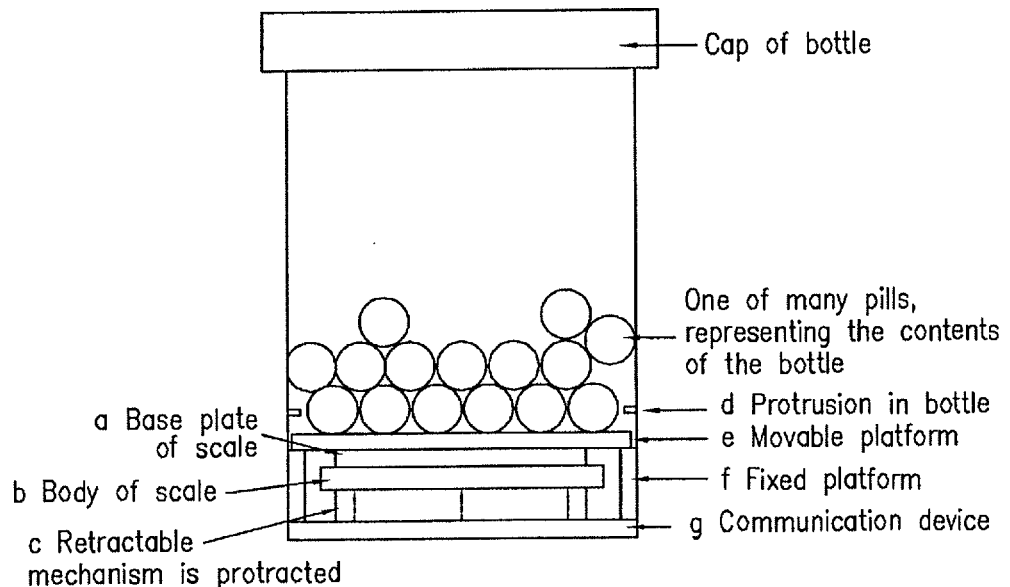

In some embodiments, sensor(s) 116 of medication container 102 may include other types of sensor(s) including, for example, weight sensors that detect the weight of medication within medication container 102 (e.g., as shown in FIGS. 10A and 10B), resistive sensors, and/or inductive sensors. Additional details regarding medication containers 102 and sensors 116 in accordance with some embodiments of the present disclosure are described below in connection with, for example, FIGS. 2-10B.

In some embodiments, data indicative of the quantity of medication within medication container 102 may be compared to data indicative of an expected quantity of medication within container 102. Based at least in part on the comparison, system 100 (e.g., backend system 104 and/or medication container 102) may provide one or reminders and/or alerts to the patient to take the medication. In some embodiments, data indicative of an expected quantity of medication remaining in a medication container 102 assigned to a given a patient may be determined based at least in part on data indicative of a date and/or time the patient filled or picked-up the medication, an original quantity of medication dispensed to the patient, the patient's medication regimen (e.g., dose size and number of doses per day), and/or the date and/or time that sensor(s) 116 measured the quantity of medication remaining within medication container 102. In some embodiments, this comparison may be performed by backend system 104 based on data stored in memory 120 and/or by other computer(s) (e.g., patient's cellular phone 128). In some embodiments, this comparison may be performed by processor(s) 110 in medication container 102 based on information stored in memory 112.

System 100 may provide different types of reminders and/or alerts to patents according to various embodiments. In some embodiments, backend system 104 may trigger the initiation of a telephone call (e.g., automated message or live operator) to a telephone number associated with the patient (e.g., a telephone number stored in memory 120 in association with a data record for the patient) when system 104 and/or medication container 102 determines that the patient has not adhered to the patient's medication regimen. In some embodiments, the telephone call may be initiated to the patient's home, cellular, and/or work telephone, and/or to a telephone number associated with the patient's physician (e.g., physician computer 132), family member, and/or other designee. Alternatively or additionally, in some embodiments, backend system 104 may trigger an electronic message, such as a text message, email, or other digital message to the patient (e.g., patient's cell phone 128), patient's physician (e.g., physician computer 132), and/or patient's designee, as indicated by instructions stored in memory 120. In some embodiments, medication container 102 triggers the issuance of reminders and/or alerts to the patient, for example, via one or more alerts 124 of medication container 102 and/or via communication with (e.g., text message to) a user computer 128.

In some embodiments, medication container 102 may issue one or more alerts 124 when system 104 and/or medication container 102 determines that the patient has not adhered to the patient's medication regimen. For example, medication container 102 may include one or more light source(s) 124 (e.g., light emitting diodes (LEDs)) that light up when the patient fails to adhere to the patient's medication regimen. For example, a light source may light up a certain color or in a blinking pattern, and/or have differing lights or lighting patterns for different circumstances (e.g., a patient forgetting to take medication, lack of connectivity to backend server 104, or light of increasing intensity or amount the longer a patient fails to take a medication dose). Light source(s) 124 may be positioned at any suitable location(s) on or in medication container 102, including on different areas of a body and/or cap. In some embodiments, medication container 102 may include words or symbols above specific lights such as, for example, "not connected" or "take a dose."

Alternatively or additionally, medication container 102 may include other types of alert(s) 124, including for example a graphical and/or text display for displaying text and/or graphics (e.g., text and/or graphics received automatically from backend system 104) and/or a speaker for issuing audio alerts. With respect to audio alerts, in some embodiments a medication container 102 play different sounds, sound patterns, and/or volumes for different circumstances (e.g., a patient forgetting to take medication, lack of connectivity to backend server 104, or sound of increasing intensity the longer a patient fails to take a medication dose). In some embodiments, medication bottle 102 may play a voice alert (e.g., patient's voice, family member's voice, and/or doctor's voice). The voice alert may be stored in memory 114. The voice alert may be recorded and downloaded to memory 114 using any suitable approach (e.g., a user dialing a telephone number and recording the voice alert, which is then downloaded via USB or a wireless connection to medication container 102).

In some embodiments, instructions for medication container 102 to activate the light(s) and/or other alerts of medication container 102 may be provided by backend system 104, other computer(s) (e.g., user computer 128), and/or medication container 102. For example, such instructions may be provided based at least in part on the above-described data indicative of an expected medication quantity for the patient and data indicative of a measured medication quantity remaining within container 102. In some embodiments, backend system 104, other computer(s), and/or medication container 102 may store non-transitory computer executable program instructions in memory for implementing a reminder/alert escalation chain for medication adherence, whereby a patient who does not take medicine as expected is reminded (e.g., with different and/or multiple reminders/alerts) until he or she removes the appropriate amount of medication from medication container 102.

System 100 may adaptively provide different types of reminders and/or alerts, or timing of reminders or alerts, based on a patient's past adherence statistics (e.g., stored in memory 114 and/or 120 or in memory of user computer 128). For example, in some embodiments, backend system 104, other computer(s) such as user computer 128, and/or medication container 102 may utilize one or more machine learning techniques to determine when, and which type, of reminders to initiate to a patient and/or when a patient is most likely to take his or her medication. For example, the timing or type of reminders may change depending on when system 100 predicts that the patient is most likely to take his or her medication (e.g., the prediction being based at least in part on the day of the week, number of dosages, etc.). In some embodiments, reminders are initiated to patients at times when stored past data indicates that the patient is most likely to open or close medication container 102 (e.g., morning between 7 and 8 am, in afternoon hour(s), or evening hour(s)).

In some embodiments, system 100 (e.g., medication container 102 and/or backend server 104) may trigger reminders and/or alerts to a patient based at least in part on data received from a patient's computer or phone 128. For example, phone input such as a text message to backend system 104 (e.g., indicating for example medication compliance or non-compliance) may, at least in part, cause backend system 104 to trigger a reminder or alert (e.g., displayed on or otherwise issued by medication container 102) for the patient to perform a function such as taking medication or obtaining a refill. As another example, input (or lack of input) into an application running on user computer 128 may cause user computer 128 to issue or otherwise trigger a reminder and/or alert to the patient.

Medication container 102 may measure and record the quantity of medication within container 102 and/or report that information to backend server 104 and/or other computer(s) (e.g., user computer 128) at any suitable time or according to any suitable frequency (e.g., continuously or substantially continuously). For example, in some embodiments, medication container 102 may include one or more sensors 126 for detecting when a user has closed or opened a cap of container 102. In some embodiments, a sensor 126 may include a switch that is activated (e.g., pressed down) when the cap is closed, thus signaling that the patient might have just removed medication from the container. After the switch is activated (e.g., immediately after the switch is activated or at another time), medication container 102 may measure and record a measurement from sensor(s) 116 indicative of the quantity of medication within the container and/or communicate that measurement to backend system 104.

In some embodiments, medication container 102 may wait a predetermined time (e.g., between 5 and 10 seconds) after a sensor 126 is activated to measure, record, and/or the report back to backend server 104 the data indicative of the quantity of medication within container 102. In some embodiments, non-transitory computer program instructions (computer logic) stored in memory 114 may be utilized by processor(s) 110 to control this timing function of medication container 102. For example, medication container 102 may only measure, record, and/or report back a measurement to backend server 104 if the switch remains activated (the cap remains closed) a predetermined time period after the switch was originally activated. This may prevent container 102 from measuring, recording, and/or reporting back a measurement when a patient accidentally activates the switch (e.g., presses the switch with the patient's finger) before the patient has removed any medication. In some embodiments, medication container 102 may store measurement(s) in memory 114, and may retry to communicate measurement data to backend system 104 and/or other computer(s) if and when an original attempt to communicate the data fails (e.g., due to noise in a communications channel or for any other reason).

In some embodiments, medication container 102, backend server 104, and/or other computer(s) (e.g., user computer 128) may trigger reminders and/or alerts to the patient based at least in part on sensor(s) 126 sensing the closing and/or opening of a cap of medication container 102. For example, if medication container 102, backend server 104, and/or other computer(s) determine that a predetermined amount of time has lapsed since the cap was last opened and/or closed (e.g., a time that exceeds the time between doses according to stored data indicative of a patient's medication regimen), medication container 102, backend server 104, and/or other computer(s) may trigger reminder(s) and/or alert(s) to the patient to take their medication (e.g., light source activation, graphical display, text message, audio alert, telephone call, etc.).

In some embodiments, sensor(s) 116 may measure the contents of medication container 102 at specific times of day (e.g., every day at 8 am and 8 pm), set intervals (e.g., every 4 hours), time since the last change (e.g., 5 minutes since the container was moved), bundled within a short time period, initiated upon an action, triggered by the user or a third party, triggered remotely by a system operator within backend system 104, and/or triggered by an application running on user computer 128. In some embodiments, single measurements may be taken when the device is being moved, changing environments, and/or in other ways changed or handled. In some embodiments, multiple or a combination of these mechanisms may be utilized, which may improve the confidence and accuracy of the system.

It is appreciated that in some embodiments of the present disclosure, transitory readings may not be indicative of the steady-state contents of medication container 102 and may lead to misleading or inaccurate measurements and conclusions. Accordingly, in some embodiments, measurements of the container contents are bundled to ensure that this does not occur. For example, several sensory readings may be performed by sensor(s) 116 within a short amount of time to allow system 100 to validate and confirm that the measurement is accurate. If multiple readings within a given time window do not agree (e.g., as determined by one or more processor(s) in medication container 102, backend server 104, and/or other computer(s) such as a personal computer 128), the patient may be alerted (e.g., via one or more alerts 124) to change the conditions of the container to enable a more accurate reading. The patient can then make the necessary corrections and initiate a new measurement (e.g., either automatically by sensing the container has been moved again, or based on other factors like set time duration between notification). The process may be repeated until it is determined that an accurate measurement has been collected. Often containers are moved or in strange positions and if there are changes in the readings between short time periods, the system is able to sense the expected irregularity, note the potential problem, alert the proper party, and re-initiate a measurement when deemed appropriate.

In some embodiments, the system is aware of how long a substance has resided in the container as compared to its expiration date (e.g., based on data stored in memory 114 or memory 120. This may be determined by one or more processor(s) in medication container 102, backend server 104, and/or other computer(s) such as a personal computer 128. Accordingly, in some embodiments, the system is able to alert the patient (or designated contact) for the substance to be discarded or replaced using any of the alert mechanisms described above and/or other alert(s).

Medication container 102 may include different types of sensor(s) 126 in various embodiments. For example, in some embodiments, sensor 126 may include a detector switch for detecting engagement with a container cap and for outputting a signal or data indicative of an open or closed state. In some embodiments, sensor 126 may include an ultrasonic sensor engagement for sensing an open or closed state for the container cap. In other embodiments, sensor 126 may include a proximity probe sensor, photo interrupter, optical switch, and/or other trigger mechanism for detecting an open or closed state of the container cap.

In some embodiments, medication container 102, backend server 104, and/or other computer(s) may trigger reminders and/or alerts to the patent based at least in part on a proximity of medication container 102 to a user computer 128 (e.g., patient's cellular phone), a location (e.g., patient's home), or an intermediate device (e.g., wall-mountable dedicated base station in the patient's home). For example, an application running on medication container 102 (e.g., including computer executable instructions stored in memory 112) may cause container 102 to check or ping wirelessly (e.g., periodically or at any other suitable time) for the presence of a cellular phone or intermediate device (e.g., dedicated base station plugged into a wall outlet), which may also be running an application for receiving and monitoring for such communications. As another example, a global positioning module in medication container 102 may check (e.g., periodically or at any other suitable time) whether a location of the bottle matches a location stored in memory. In some embodiments, a global positioning module in medication container 102 may register the location(s) where medication container 102 is opened and closed. Such location data may be stored in memory 114, communicated to backend system 104 for storage in memory 120, and/or communicated to other computer(s) (e.g., user computer 128).

In some embodiments, reminders and/or alerts to the patient may be triggered based at least in part on proximity of a user computer 128 (e.g., patient's cellular phone) to medication container 102, a location (e.g., patient's home), or an intermediate device (e.g., wall-mountable dedicated base station in the patient's home). For example, an application running on user computer 128 (e.g., including computer executable instructions stored in memory of computer 128) may cause user computer 128 to check or ping wirelessly (e.g., periodically or at any other suitable time) for the presence of medication container 102 or an intermediate device, which may also be running an application for receiving and monitoring for such communications. As another example, a global positioning module in user computer 128 may check (e.g., periodically or at any other suitable time) whether the location of the phone matches a location stored in memory.

In some embodiments, medication container 102 may utilize an open or other application programming interface (API). This may allow other devices and systems (e.g., backend system 104, user computer 128, and/or a pharmacy's computer 130) to communicate with medication container 102 in a more efficient and user-friendly manner.

Medication container 102 may have any suitable size and/or shape. For example, in some embodiments, medication container 102 may be a pill bottle. In some embodiments, the pill bottle may have a cylindrical or substantially cylindrical body as with conventional pill bottles. The body may have a circular or substantially circular cross section. The cap of medical container 102 may be circular or substantially circular in cross-section for affixation to the body. In its normal and upright position, the body may extend vertically from a base of the container, the base having a circular or substantially circular cross-section, up to the cap. In other embodiments, a body of medication container 102 may be non-cylindrical (e.g., square, elliptical, conical, rectangular, or in decorative, ergonomic, or child-friendly shapes or figures). In some embodiments, medication container 102 may have a clamshell shape.

In some embodiments, medication container 102 may have multiple compartments. For example, a pill or liquid medication bottle may be split or divided (e.g., in half or in some other proportionality), such that electrical circuitry (e.g., cellular modem and/or microprocessor, etc.) is housed in one or more electronics compartments that are separated from but coupled to a compartment for the actual medication. In some embodiments, the split or division exists along only a part of the pill bottle (e.g., only half-way from the bottom), to allow the container to house more medication. In some embodiments, the division of medication container 102 may ensure that medication does not come into direct physical contact with the electrical circuitry of the container.

In some embodiments, medication container 102 may have a conical configuration within the medication compartment to cause medication to gather at the bottom of the container in a specification manner (e.g., near sensor(s) 116).

In some embodiments, medication container 102 may include stickers or other identifiers that affix to a cap and/or body of the container. Such identifiers may function to indicate to whom the container belongs.

In some embodiments, medication container 102 may include gripping material (e.g., rubber or ribbed plastic) on at least a portion of the container such as the body and/or cap to make the container easier to hold.

In some embodiments, medication container 102 may be large enough to house a multi-day medication container that fits at least partially into it (e.g., a conventional, off-the-shelf pill box available for purchase at a local pharmacy that contains multiple compartments, typically one compartment for each day of the week). In some embodiments, medication container 102 may include one or more sensor(s) 116 for sensing when medication is removed from any of the compartments within the multi-day medication container.

In some embodiments, medication container 102 may include one or more functionalities directed to power management. For example, in some embodiments, container 102 may include a mini-USB/micro-USB charger, or other charging capability for charging a local power source 110. Local power source 110 (e.g., battery) may include any suitable type and/or shape. In some embodiments, medication container 102 may include a retractable charger in or coiled around a portion (e.g., bottom) of the container that is configured to plug into a wall outlet. In some embodiments, some or all of the electronics within medication container 102 (e.g., a receiver) may power up periodically or according to any other suitable schedule or impetus (e.g., once every X amount of time or via an external prompt). This may allow container 102 to conserve power, allowing it to selectively turn on to receive reminders (e.g., from backend system 104 once every X amount of time) and/or to receive and/or process signals and/or data. In some embodiments, medication container 102 may include two or more connectivity options having different power consumption levels associated therewith for communicating with backend server 104 and/or other computer(s) (e.g., via Bluetooth, 2G, or 3G). Medication container 102 may initially seek to utilize a less power-intensive mode of connectivity to send out signal(s) to backend server 104 or another device such as a patient's cellular phone 128 (e.g., Bluetooth), and only if it is unable to connect will it use another, more power-intensive mode (e.g., 3G). In some embodiments, medication container 102 may include an ON-OFF button or switch. For example, once turned on, the bottle may not be able to be turned off by a patient. This may allow a pharmacist to turn the bottle on (e.g., when ready for use or once it is charged), and may conserve power because the container will not drain the local power source as it sits on the store shelf or in storage awaiting assignment to a patient.

In some embodiments, medication container 102 may include one or more features that identify or associate the container with, for example, a patient, a data record, and/or a transmitter or transceiver 108 in the container. For example, in some embodiments, medication container 102 may include a barcode or other identifier (e.g., fixed to or printed on an outer portion of the container). In some embodiments, the identifier may be associated with an account number for the patient or a particular module (e.g., 3G module) inside the container. In some embodiments, the identifier may be recorded (e.g., scanned) by a pharmacist to associate the medication container 102 and its unique identifier with a data record for a particular patient. Data associating the identifier for medication container 102 with the particular patient may be stored in, for example, memory 120 of backend system 104, memory 114 of medication container 102, and/or in memory of pharmacy computer 130, physician computer 132, and/or user computer 128. In some embodiments, the identifier may be included in communication(s) between medication container 102, on one hand, and backend system 104 and/or other computer(s) (e.g., 128, 130, and/or 132) on the other hand. For example, medication container 102 may communicate data packet(s) to backend server 104 and/or other computers, where the data packet(s) include data indicative of the identifier and/or data indicative of a medication quantity, such as data indicative of a capacitance measurement between interleaved or interdigitated electrodes positioned at least partially around a body of the container.

In some embodiments, memory 120 and/or memory 114 (and/or other memory of computers 128, 130, and/or 132) may store non-transitory computer program instructions (computer logic) for causing computer(s) or processor(s) within medication container 102, backend server 104, and/or other computers to associate the identifier for the container with a prescription drug/dosage/refill schedule, patient contact information (e.g., preferred type(s) of reminder(s) and/or alert(s)), doctor contact information, pharmacy contact information, and/or any other information associated with a data record for a patient including the information described above (e.g., data indicative of medication quantities remaining within container 102, data indicating time since the last medication quantity measurement from container 102, etc.), and/or to initiate reminder, alert, and/or other functions based on this information. In some embodiments, backend server 104 and/or other computer(s) may access stored patient data to determine whether, when, and/or how to contact a patient with reminder(s) and/or alert(s) to take medication.

In some embodiments, medication container 102 may include a button or other user-input feature or option (e.g., on a portion of a cap or body, or on or near where a cap screws into the body) that triggers a medication refill. For example, when a user activates the user-input feature, medication container 102 may communicate with backend server 104, a computer associated with the patient's doctor or family member 132, and/or a pharmacy computer system 130 that the patient has requested a refill.

In some embodiments, medication container 102 may include a button or other user-input feature or option (e.g., on a cap or body, or on or near where a cap screws into the body) that allows a patent to alert or speak with someone (e.g., doctor or family member). For example, activating this option for a certain period of time may elicit a certain response (e.g. holding it for 10 seconds causes a doctor to be notified to call the patient). When a user activates this user-input feature, medication container 102 may communicate with backend server 104, a computer associated with the patient's doctor or family member 132, and/or a pharmacy computer system 130 that the patient is requesting assistance.

In some embodiments, medication container 102 may include one or more security features. For example, medication container 102 may include a fingerprint scanner, touch pad for use in entering a code, and/or other lock mechanism. In some embodiments, such mechanism(s) may be used to restrict access to the medication contained within medication container 102 and/or other features (e.g., refill function, assistance request function, etc.).

In some embodiments, backend system 104 may solicit feedback from patients (e.g., via text message, email, and/or telephone calls to patients) to determine reasons for non-adherence and/or may respond accordingly to such feedback using any suitable approach (e.g., text or email acknowledgement). In some embodiments, such feedback may be stored in a data record for the patient and utilized by the above-described machine learning techniques to more accurately predict likelihood of patient non-adherence and/or to select appropriate reminders and/or alerts.

Figure 2A:
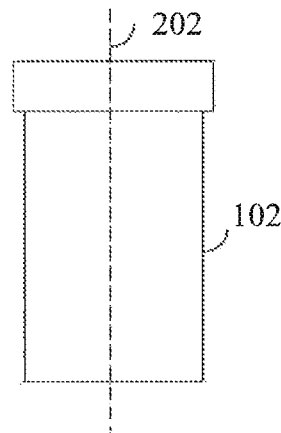
FIGS. 2A-2C illustrate a medication container that includes a two-electrode capacitance sensor for measuring the contents of the container according to some embodiments of the present disclosure.
Figure 2B:
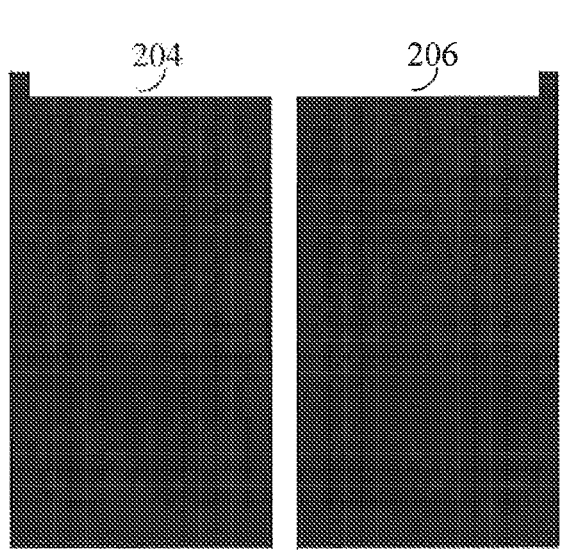
Figure 2C:
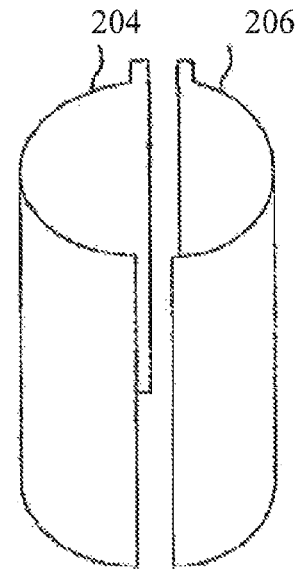

FIGS. 2A-2C illustrate a medication container 102 that includes a two-segmented capacitance sensor 116 according to some embodiments of the present disclosure. FIG. 2A shows a side view of a conventionally-shaped, generally cylindrical medication container 102 (e.g., pill bottle). In the example shown, medication container 102 includes a central axis 202 that extends vertically from a base of the container when the container is in its normal and upright position. For example, and without limitation, the container may have a cap diameter of approximately 31 millimeters (mm) (as measured perpendicularly to axis 202), a body diameter of approximately 29.5 mm, and a height of approximately 68 mm (as measured in a direction parallel to axis 202). Other sizes and/or shapes for medication containers 102 may be utilized in other embodiments of the present disclosure.

FIG. 2B illustrates a flat or unrolled view of an electrode pattern for a two-segmented capacitance sensor 116, including a first conductive terminal 204 in electrical communication with a first electrode and a second conductive terminal 206 in electrical communication with a second electrode. In the example shown, the electrodes are conductive blocks that extend from terminals 204 and 206, although other shapes for the electrodes may be utilized in other embodiments (e.g., triangle, oval, part-circular, tubular, and/or amorphous electrodes). In some embodiments, electrical connection of the electrodes to, for example, a capacitance to digital converter 118 (FIG. 1) or another electrical circuit, may be made via at least a portion of the first and second terminals 204 and 206 (e.g., via the small protrusions of terminals 204 and 206 shown in FIG. 2B).

FIG. 2C illustrates the electrodes of the two-segmented capacitance sensor 116 of FIG. 2A as configured for positioning on or in at least a portion of medication container 102. For example, the electrodes may be positioned around at least part of, a substantial portion of, most of, or a substantially entirety of a circumference of the body of the container. In the example shown, terminals 204 and 206 and their associated electrodes are opposed but are not interleaved or interdigitated. At most only one of the terminals/electrodes 204 and 206 is present at any given point around the circumference of the medication container. The capacitor formed by the electrodes is similar to, for example, a parallel-plate capacitor.

Figure 3A:
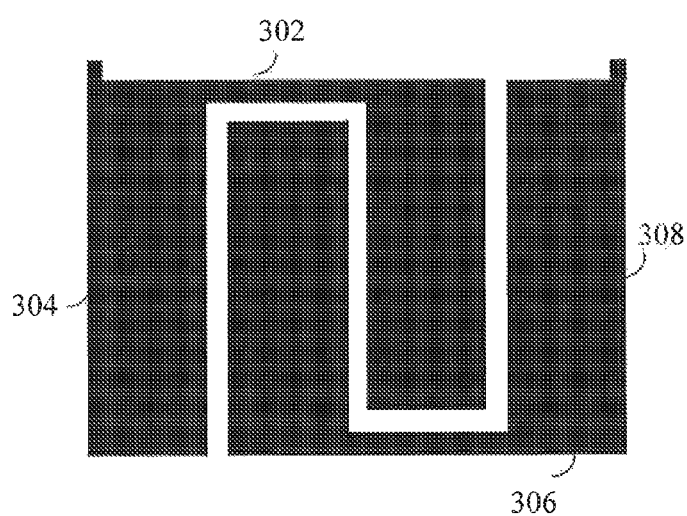
FIGS. 3A, 3B, 4A, and 4B illustrate capacitance sensors that include vertically-oriented interleaved or interdigitated electrodes for measuring the contents of a medication container according to some embodiments of the present disclosure.
Figure 3B:
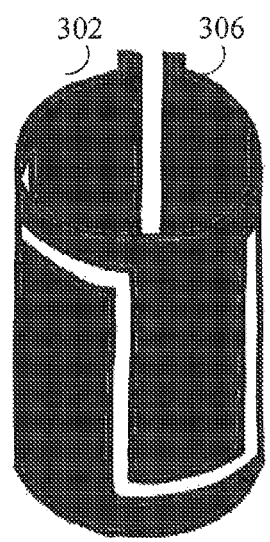

FIGS. 3A and 3B illustrate an embodiment of a capacitance sensor 116 for a medication container, where the capacitance sensor includes vertically-oriented interleaved or interdigitated electrodes. For example, for a medication container 102 of the type shown in FIG. 2A, a direction of elongation of the electrodes may be parallel to central axis 202. FIG. 3A illustrates a flat or unrolled view of an electrode pattern for the capacitance sensor, including a first terminal 302 in electrical communication with one or more electrodes 304 (e.g., 2 electrodes in the embodiment shown in FIGS. 3A and 3B) and a second terminal 306 in electrical communication with one or more electrodes 308 (e.g., 2 electrodes in the embodiment shown in FIGS. 3A and 3B).

FIG. 3B illustrates the electrodes as configured for positioning on or in at least a portion of medication container 102 (e.g., positioned around at least part of, a substantial portion of most of, or a substantially entirety of a circumference of the body of the container). In the example shown, electrodes 304 and 308 are interleaved/interdigitated in an alternating pattern, with at least one electrode 304 being positioned in between two electrodes 308, or vice versa. Generally, the inclusion of multiple (e.g., 4) interleaved electrodes, instead of the 2 opposed electrodes in the configuration of FIGS. 2B-2C, improves the ability to accurately and repeatably measure the contents of medication container 102 by measuring capacitance. Generally, with the exception of the left-most and right-most regions of the electrode pattern shown in FIG. 3A, at least a portion of (i) terminal 302 and/or electrode 304 and (ii) terminal 306 and/or electrode 308 is present at any given point around the circumference of the medication container. In other embodiments, the terminals and/or electrodes may be shaped differently (e.g., triangle, ovular, part-circular, tubular, and/or amorphous, etc.), have different sizes (e.g., length and/or thickness), and/or may be positioned in different configurations relative to medication container 102 (e.g., different angular configuration(s) relative to axis 202). The space between the opposed electrodes in FIGS. 3A and 3B resembles a square wave. In other embodiments, other numbers and/or configurations of electrodes may be provided within capacitance sensor 116.

Figure 4A:
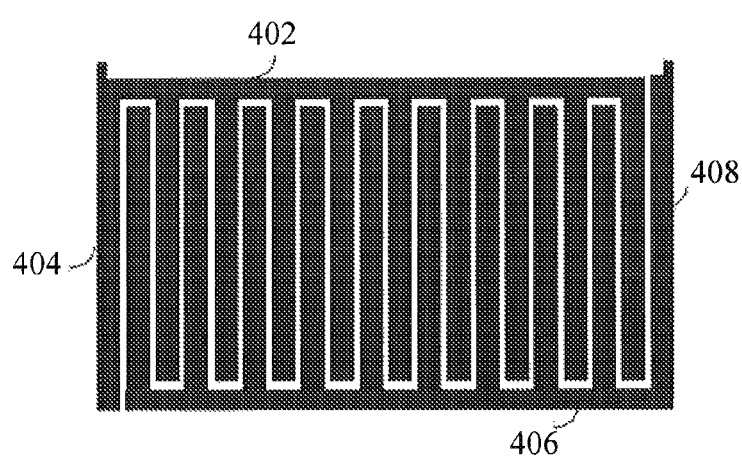
Figure 4B:

FIGS. 4A and 4B illustrate another embodiment of a capacitance sensor 116 where the capacitance sensor includes vertically-oriented interleaved or interdigitated electrodes. For example, for a medication container 102 of the type shown in FIG. 2A, a direction of elongation of the electrodes may be parallel to central axis 202. FIG. 4A illustrates a flat or unrolled view of an electrode pattern for the capacitance sensor, including a first terminal 402 in electrical communication with one or more electrodes 404 (e.g., 10 electrodes in the embodiment shown in FIGS. 4A and 4B) and a second terminal 306 in electrical communication with one or more electrodes 308 (e.g., 10 electrodes in the embodiment shown in FIGS. 4A and 4B). FIG. 4B illustrates the electrodes as configured for positioning on or in at least a portion of medication container 102 (e.g., positioned around at least part of, a substantial portion of, most of or a substantially entirety of a circumference of the body of the container). In the example shown, electrodes 404 and 408 are interleaved/interdigitated in an alternating pattern, with at least one electrode 404 being positioned in between two electrodes 408, or vice versa. Generally, with the exception of the left- and right-most regions of the electrode pattern shown in FIG. 4A, at least a portion of (i) terminal 402 and/or electrode 404 and (ii) terminal 406 and/or electrode 408 is present at any given point around the circumference of the medication container. In the example shown, the vertical electrodes in FIGS. 4A and 4B have a reduced thickness in comparison to the vertical electrodes shown in FIGS. 3A and 3B.

Figure 5A:
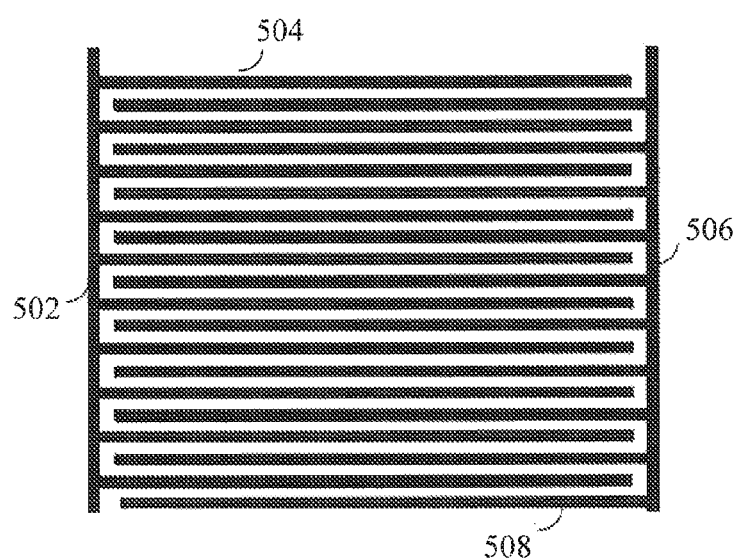
FIGS. 5A and 5B illustrate a capacitance sensor that includes horizontally-oriented interleaved or interdigitated electrodes for measuring the contents of a medication container according to some embodiments of the present disclosure.
Figure 5B:
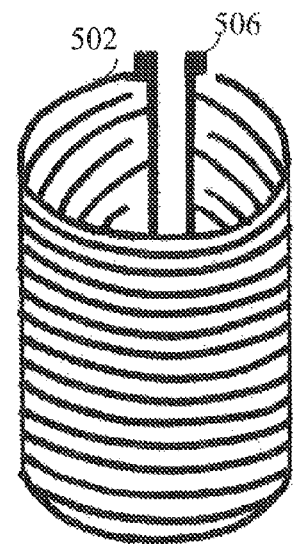

FIGS. 5A and 5B illustrate an embodiment of a capacitance sensor 116 for a medication container, where the capacitance sensor includes horizontally-oriented interleaved or inter-digitated electrodes. For example, for a medication container 102 of the type shown in FIG. 2A, a direction of elongation of the electrodes may be perpendicular to central axis 202. FIG. 5A illustrates a flat or unrolled view of an electrode pattern for the capacitance sensor, including a first terminal 502 in electrical communication with one or more electrodes 504 (e.g., 10 electrodes in the embodiment shown in FIGS. 5A and 5B) and a second terminal 506 in electrical communication with one or more electrodes 508 (e.g., 10 electrodes in the embodiment shown in FIGS. 5A and 5B). FIG. 5B illustrates the electrodes as configured for positioning on or in at least a portion of medication container 102 (e.g., positioned around at least part of, a substantial portion of most of or a substantially entirety of a circumference of the body of the container). In the example shown, electrodes 504 and 508 are interleaved/interdigitated in an alternating pattern, with at least one electrode 504 being positioned in between two electrodes 508, or vice versa. Generally, with the exception of region at or close to terminals 502 and 506, at least a portion of (i) an electrode 504 and (ii) and electrode 508 is present at any given point around the circumference of the medication container.

FIGS. 6A and 6B illustrate yet another embodiment of a capacitance sensor 116 for a medication container, where the capacitance sensor includes vertically-oriented interleaved or interdigitated electrodes. For example, for a medication container 102 of the type shown in FIG. 2A, a direction of elongation of the electrodes may be parallel to central axis 202. FIG. 6A illustrates a flat or unrolled view of an electrode pattern for the capacitance sensor, including a first terminal 602 in electrical communication with one or more electrodes 604 (e.g., 6 electrodes in the embodiment shown in FIGS. 6A and 6B) and a second terminal 606 in electrical communication with one or more electrodes 608 (e.g., 6 electrodes in the embodiment shown in FIGS. 6A and 6B). FIG. 6B illustrates the electrodes as configured for positioning on or in at least a portion of medication container 102 (e.g., positioned around at least part of, a substantial portion of, most of, or a substantially entirety of a circumference of the body of the container). In the example shown, electrodes 604 and 608 are interleaved/interdigitated in an alternating pattern, with at least one electrode 604 being positioned in between two electrodes 608, or vice versa. Generally, with the exception of the left-most and right-most regions of the electrode pattern shown in FIG. 6A, at least a portion of (i) terminal 602 and/or electrode 604 and (ii) terminal 606 and/or electrode 608 is present at any given point around the circumference of the medication container. In the example shown, the vertical electrodes in FIGS. 6A and 6B have different shape than the electrodes shown in FIGS. 3A, 3B, 4A, and 4b. In FIGS. 6A and 6B, the electrodes and terminals have smoothed edges. The space between the opposed electrodes in FIGS. 6A and 6B resembles a sine wave.

Figure 7A:
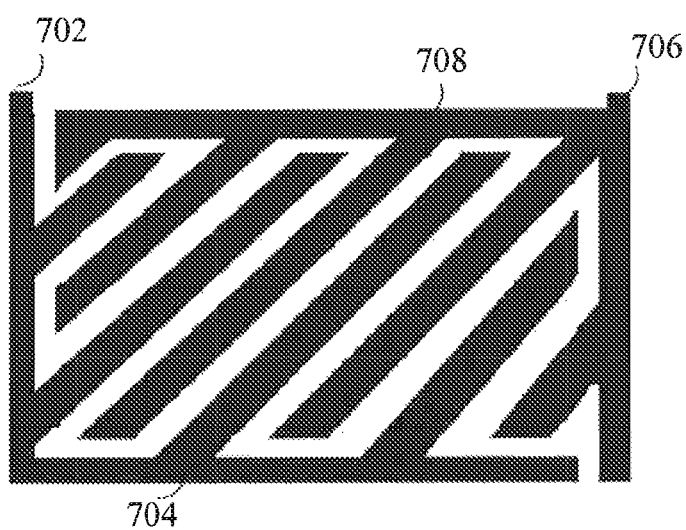
FIGS. 7A and 7B illustrate a capacitance sensor for a medication container that includes diagonally-oriented interleaved or interdigitated electrodes according to some embodiments of the present disclosure.
Figure 7B:

FIGS. 7A and 7B illustrate yet another embodiment of a capacitance sensor 116 for a medication container, where the capacitance sensor includes diagonally-oriented interleaved or interdigitated electrodes. For example, for a medication container 102 of the type shown in FIG. 2A, a direction of elongation of the electrodes may be at a 45 degree angle to central axis 202. Other angular relationships for one or more (e.g., all) of the electrodes may be utilized in other embodiments of the present disclosure (e.g., between 0 and 30 degrees, between 30 and 60 degrees, and between 0 and 90 degrees). FIG. 7A illustrates a flat or unrolled view of an electrode pattern for the capacitance sensor, including a first terminal 702 in electrical communication with one or more electrodes 704 and a second terminal 706 in electrical communication with one or more electrodes 708. FIG. 7B illustrates the electrodes as configured for positioning on or in at least a portion of medication container 102 (e.g., positioned around at least part of, a substantial portion of, most of, or a substantially entirety of a circumference of the body of the container). In the example shown, electrodes 704 and 708 are interleaved/interdigitated in an alternating pattern, with at least one electrode 704 being positioned in between two electrodes 708, or vice versa.

Capacitance sensor(s) 116 may have additional electrodes and/or terminals according to some embodiments of the present disclosure. For example, in some embodiments, an additional terminal may be positioned on or in a bottom surface of medication container 102 (e.g., a circular conductive terminal) for use in measuring capacitance. Capacitance may be measured between, for example, the bottom terminal and the first terminal or second terminal in any of the above-described embodiments (e.g., first terminal 402 in the embodiment shown in FIGS. 4A and 4B). This may allow for increased accuracy in the measurement of the quantity of medication (e.g., pills or liquid medication) at the bottom of the container or when the container only includes a small number of pills. In some embodiments, computer executable instructions stored in memory 114 of medication container 102 alter the terminal pairs between which the capacitance is measured depending on, for example, the quantity of medication in the container.

In some embodiments, capacitance sensor(s) 116 may include a terminal and electrode within medication container 102 (e.g., along all or a portion of central axis 202 in FIG. 2A) for use in measuring capacitance. Capacitance may be measured between, for example, this terminal (e.g., located on or in a bottom surface of medication container 102) and the first terminal or second terminal in any of the above-described embodiments (e.g., first terminal 402 in the embodiment shown in FIGS. 4A and 4B). Such an additional electrode may allow a larger portion of the medication within container 102 to be located between electrodes and may improve accuracy of the measurement.

Figure 8:
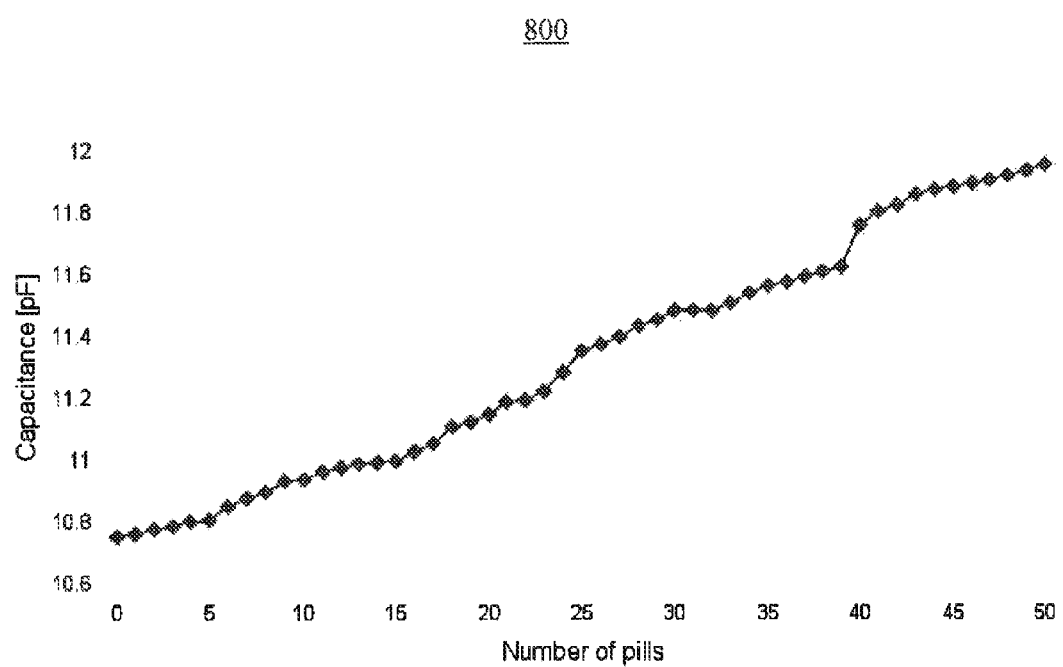
FIG. 8 is a graph of measured capacitance versus number of pills in a medication container as measured by a capacitance sensor in accordance with an embodiment of the present disclosure.

FIG. 8 is a graph of capacitance (y-axis) versus number of pills (x-axis) as measured by a capacitance sensor 116 in accordance with an embodiment of the present disclosure. In this example, capacitance sensor 116 was constructed as shown in FIGS. 3A and 3B. As shown, the capacitance measurement ranges from slightly less than 10.7 picoFarads (pF) to slightly less than 12 pF as the contents of medication container 102 change from 0 pills to 50 pills, respectively. In this example, the pills were Aspirin 325 milligram (mg) pills, although other sizes and types of pills (or liquid medication) may be used in other embodiments. As shown, the capacitance varies generally linearly with pill count, with each pill producing a change in capacitance of approximately 24 femtoFarads (fF) in this example. This is within the range of available capacitance controllers (e.g., capacitance to digital converter 118 (FIG. 1)). In this experiment, measurements were taken using an evaluation kit for controller AD7746 from Analog Devices. In other embodiments, depending on the configuration of capacitance sensor 116, and the types of pills housed within medication container 102, each pill may produce a change in capacitance of between approximately 10 fF and 100 fF or more (e.g., between 20-40 fF).

FIG. 9 is a graph of capacitance (y-axis) versus volume of liquid medication (x-axis) as measured by a capacitance sensor 116 in accordance with an embodiment of the present disclosure. In this example, capacitance sensor 116 was constructed as shown in FIGS. 6A and 6B. As shown, the capacitance measurement ranges from slightly greater than 7 picoFarads (pF) to about 19.5 pF as the contents of medication container 102 change from 0 milliliters (mL) to 35 mL. In this example, the liquid medication was liquid tussin, although other types of liquid medication may be used in other embodiments. As shown, the capacitance varies generally linearly with quantity of liquid medication. In this example, the measurements marked with a circle were measured with a first offset, and the measurements marked with a square were measured with a second offset, as applied to the capacitance controller (Analog Devices AD7746). These different offsets were the reason for the equivalence or slight dip in capacitance measurements between the tenth and eleventh measurements, and can be overcome in practice with additional calibrations during measurement. As shown, on average each milliliter of liquid medication produces a change in capacitance of about 350 fF. In other embodiments, depending on the configuration of capacitance sensor 116, and the type of liquid medication housed within medication container 102, each milliliter of medication may produce a change in capacitance of between approximately 100 and 500 fF or more (e.g., between 250-450 fF).

FIGS. 10A and 10B illustrate a medication container 102 that includes a weight sensor 116 for measuring the weight of medication within the container according to some embodiments of the present disclosure. In some embodiments, sensor 116 may utilize an integrated strain gage and gyroscope architecture to determine the container contents. FIG. 10A shows the sensor in a retracted/resting state. FIG. 10B shows the device in a protracted/active state. Pills or liquid medication rest on a movable platform (e). The movable platform rests on a fixed platform (f). The movable platform is secured from moving out of a safe position. In some embodiments, this is accomplished by having the movable platform protected on one side by the fixed platform (e), and protected on the other side by tiny protrusions in the body of the bottle (d).

In some embodiments, a weighing mechanism, such as a scale, is contained the device (a & b). The weighing mechanism is attached to a retractable mechanism (c), which rests in its retracted state. In its retracted state, the area of the weighing mechanism that determines an items mass, such as the scale's base plate (a), is below both the movable platform (e) and not in contact with any platform, material or substance whatsoever, in some embodiments. This ensures that the weighing mechanism does not experience the stress of constant weight and pressure on its components, so that the weighing mechanism stays properly calibrated. The weighing mechanism establishes baseline periodically when in the retracted state, so as to ensure accuracy.

When it is determined that the contents of the drug container should be measured (e.g., using a cap sensor as described above), the weighing mechanism rises into its protracted state as shown in FIG. 10B. As the retractable mechanism (c) rises into its protracted state, it lifts both the base plate (a) and the body of the scale (b) up so that the base plate (a) makes contact with movable platform (e). The weighing mechanism (c) continues to rise into its fully protracted state, lifting the movable platform (e) off of and above of the fixed platform (f).

When the weighing mechanism is in its fully protracted state, the movable platform (e) and the contents of the bottle fully rest on the weighing mechanism as shown in FIG. 10B. The weighing mechanism (a & b) bears the entire weight of the movable platform (e) and the contents of the bottle. In some embodiments, the total weight of the movable platform (e) and the contents of the bottle are recorded and stored by the weighing mechanism (a & b). Such information may be stored in, for example, memory 114 and/or memory 120 (FIG. 1).

Once the device has accurately recorded the weight of the platform and the contents of the bottle, the retractable mechanism (c) lowers itself and the weighting mechanism (a & b) back into its retracted state. As the weighing mechanism lowers into its retracted state, the movable platform (e) makes contact with the fixed platform (f). The retractable mechanism (c) continues to lower itself and the weighing mechanism (a & b) to a point where the base plate (a) is below the movable platform (e).

When the device is in its fully retracted state as shown in FIG. 10A, the movable platform (e) and the contents of the bottle fully rest on the fixed platform (f). The fixed platform bears the entire weight of the movable platform and the contents of the bottle. The device rests in its retracted state (e). The area of the weighing mechanism that determines an items mass, such as a scale's base plate (a), is not in contact with any platform, material or substance.

Thus, it is appreciated that the medication container 102 shown in FIGS. 10A and 10B includes a platform operatively coupled to the base, a measurement sensor 116 operatively coupled to the platform, the measurement sensor having a first position and a second position, wherein the measurement sensor is not in contact with the platform in the first position, and contacts the platform in the second position to make a measurement (e.g., weight measurement), wherein the measurement sensor resets to the first position after making a measurement in the second position.

In some embodiments, the medication container communicates the weight measurement information to a remote computer (e.g., backend system 104 or user computer 128) via its communication device (g), which may include transceiver 108 and/or processor 112 (FIG. 1).

Figure 11:
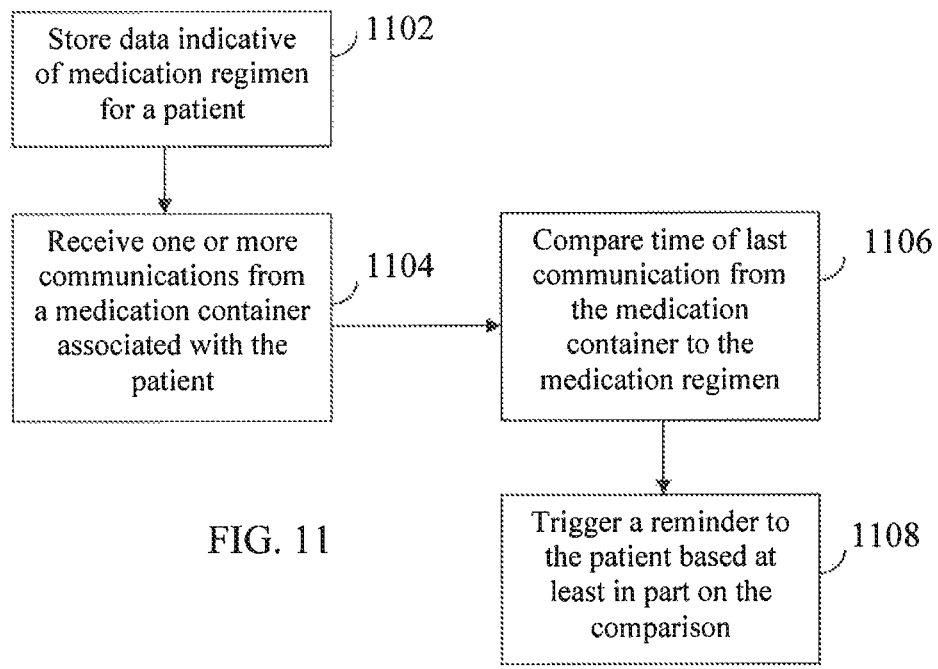
FIGS. 11 and 12 are flowcharts of illustrative methods for reminding patients to consume medication according to some embodiments of the present disclosure.

FIG. 11 is a flowchart 1100 of illustrative stages involved in a method for reminding a patient to consume a medication. At stage 1102, data indicative of a medication regimen associated with a patient may be stored in memory. At stage 1104, one or more communications from a medication container associated with the patient may be received. At stage 1106, data indicative of when a communication was last received from the medication container may be compared to the data indicative of the medication regimen associated with the patient. At stage 1108, a reminder to the patient to consume the medication may be triggered based at least in part on the comparison.

Figure 12:
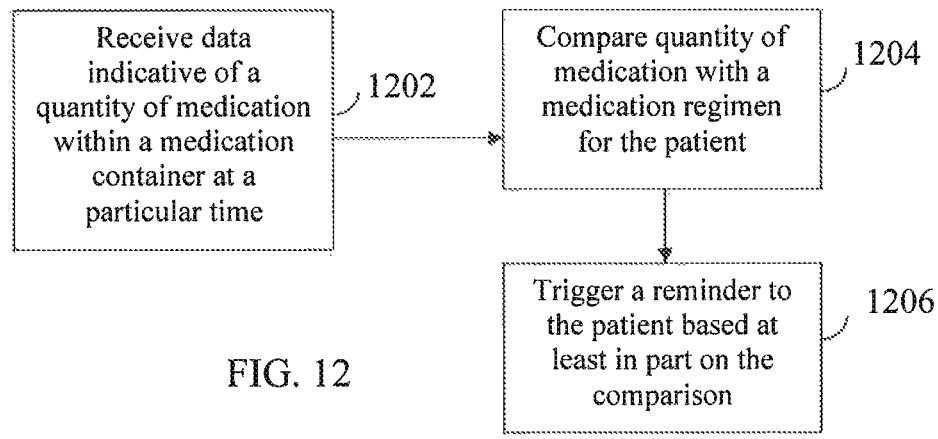

FIG. 12 is another flowchart 1200 of illustrative stages involved in a method for reminding a patient to consume a medication. At stage 1202, data indicative of a quantity of medication within the medication container at a particular time may be received. At stage 1204, the data indicative of the quantity of the medication within the medication container may be compared to data indicative of the medication regimen associated with the patient. At stage 1206, a reminder to the patient to consume the medication may be triggered based at least in part on the comparison.

The various illustrative logical blocks, modules, and circuits described in connection with the embodiments disclosed herein and shown in the figures may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions, methods, and/or applications described may be implemented in hardware, software, or firmware executed on a processor, or any combination thereof. If implemented in software, the functions may be stored on or transmitted over as one or more instructions or code on a computer-readable medium or memory. Computer-readable media include both non-transitory computer storage media and communication media including any medium that facilitates transfer of a computer program. A storage medium may be any available media that can be accessed by a computer. By way of example, and not limitation, such computer-readable media can include non-transitory computer-readable media including RAM, ROM, EEPROM, CD-ROM or other optical disk storage, magnetic disk storage or other magnetic storage devices, or any other medium that can be used to carry or store desired program code in the form of instructions or data structures and that can be accessed by a computer. A computer-readable medium can include a communication signal path. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium.

The system may include various blocks or modules as discussed above and shown in the figures. As can be appreciated by one of ordinary skill in the art, each of the modules may include one or more of a variety of sub routines, procedures, definitional statements and macros. Each of the modules may be separately compiled and linked into a single executable program. Therefore, the description of each of the modules is used for convenience to describe the functionality of the disclosed embodiments. Thus, the processes that are undergone by each of the modules may be redistributed to one of the other modules, combined together in a single module, or made available in, for example, a shareable dynamic link library.

The system may be used in connection with various operating systems such as Linux®, UNIX® or Microsoft Windows®. The system may be written in any conventional programming language such as C, C++, BASIC, Pascal, or Java, and ran under a conventional operating system. The system may also be written using interpreted languages such as Visual Basic (VB.NET), Perl, Python or Ruby.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

What is claimed is:

1. A system for reminding a patient to consume a medication, comprising:
    computer memory configured to store data indicative of a medication regimen associated with a patient; and
    one or more computers configured to receive communications from a medication container associated with the patient, the one or more computers configured to:
        receive a communication from the medication container comprising data indicative of a quantity of medication within the medication container at a given time;

compare the data indicative of the quantity of the medication within the container and data indicative of when a communication was last received by the one or more computers from the medication container to the data indicative of the medication regimen associated with the patient; and based at least in part on the comparison, trigger a reminder to the patient to consume the medication.

2. The system of claim 1, wherein the one or more computers are configured to communicate a signal to the medication container that activates an alert by the container.

3. The system of claim 1, wherein the one or more computers are configured to initiate a digital message to a user computer associated with the patient.

4. A method for reminding a patient to consume a medication, comprising:

storing in computer memory data indicative of a medication regimen associated with a patient;

receiving with one or more computers one or more electronic communications from a medication container associated with the patient, the one or more electronic communications comprising data indicative of a quantity of medication within the medication container at a given time;

comparing with the one or more computers the data indicative of the quantity of the medication within the medication container and data indicative of when a communication was last received by the one or more computers from the medication container to the data indicative of the medication regimen associated with the patient; and based at least in part on the comparison, triggering with the one or more computers a reminder to the patient to consume the medication.

5. The method of claim 4, wherein said triggering comprises communicating by the one or more computers a signal to the medication container that activates an alert by the container.

6. The method of claim 4, wherein said triggering comprises communicating by the one or more computers a digital message to a user computer associated with the patient.

* * * * *